United States Patent
Aoyagi et al.

(10) Patent No.: US 12,414,848 B2
(45) Date of Patent: Sep. 16, 2025

(54) LIVESTOCK FERTILIZED-EGG RECOVERY DEVICE

(71) Applicants: GOOD EMBRYO TECHNOLOGY INC., Hokkaido (JP); NATIONAL FEDERATION OF AGRICULTURAL COOPERATIVE ASSOCIATIONS, Tokyo (JP)

(72) Inventors: Yoshito Aoyagi, Kato-gun (JP); Makoto Takeuchi, Kato-gun (JP)

(73) Assignees: GOOD EMBRYO TECHNOLOGY INC., Hokkaido (JP); NATIONAL FEDERATION OF AGRICULTURAL COOPERATIVE ASSOCIATIONS, Tokyo (JP)

( * ) Notice: Subject to any disclaimer, the term of this patent is extended or adjusted under 35 U.S.C. 154(b) by 1183 days.

(21) Appl. No.: 17/058,456

(22) PCT Filed: May 28, 2019

(86) PCT No.: PCT/JP2019/021019
§ 371 (c)(1),
(2) Date: Sep. 21, 2021

(87) PCT Pub. No.: WO2019/230691
PCT Pub. Date: Dec. 5, 2019

(65) Prior Publication Data
US 2022/0008183 A1 Jan. 13, 2022

(30) Foreign Application Priority Data
May 31, 2018 (JP) .................................. 2018-104313

(51) Int. Cl.
*A61D 19/04* (2006.01)
*A61M 1/00* (2006.01)

(52) U.S. Cl.
CPC ............... *A61D 19/04* (2013.01); *A61M 1/71* (2021.05); *A61M 2210/1433* (2013.01)

(58) Field of Classification Search
None
See application file for complete search history.

(56) References Cited

U.S. PATENT DOCUMENTS

2016/0113680 A1* 4/2016 Hodgson ................ A61D 19/04
600/35
2017/0360478 A1 12/2017 Weichselbaum et al.

FOREIGN PATENT DOCUMENTS

JP 1-80116 U 5/1989
JP 11-19102 A 1/1999
(Continued)

OTHER PUBLICATIONS

Drost, M. (1991). Training manual for embryo transfer in water-buffaloes. Food and Agriculture Organization of the United Nations. (Year: 1991).*

(Continued)

*Primary Examiner* — Charles A Marmor, II
*Assistant Examiner* — Marc D. Honrath
(74) *Attorney, Agent, or Firm* — Birch, Stewart, Kolasch & Birch, LLP

(57) ABSTRACT

Disclosed is novel means that enables collection of embryos from the uterus of a living livestock animal, especially cattle, easily in a short time with the same accuracy as that achieved by a skilled technician. A livestock embryo collection apparatus of the present invention comprises: two syringes; a liquid transfer line for connecting a perfusate supply section-a syringe I-a balloon catheter-a syringe II-an embryo collection section; a liquid transfer direction control section for controlling the direction of transfer of a perfusate in the liquid transfer line; and a syringe pump control section for controlling pump operation of the two syringes. By this (Continued)

apparatus, injection and removal of the perfusate can be quickly carried out by simultaneous operation of the two syringes by the syringe pump control section and the liquid transfer direction control section that work in a coordinated manner, so that the working time for collection of embryos can be largely reduced, and so that embryos in the uterus of a living animal can be collected easily, quickly, and with the same accuracy as that achieved by a skilled technician.

13 Claims, 1 Drawing Sheet

(56) References Cited

FOREIGN PATENT DOCUMENTS

| JP | 2005261364 A | * | 9/2005 |
| JP | 2012-125410 A | | 7/2012 |
| KR | 20120096686 A | * | 8/2012 |

OTHER PUBLICATIONS

International Search Report, issued in PCT/JP2019/021019, dated Jun. 25, 2019.
Written Opinion of the International Searching Authority, issued in PCT/JP2019/021019, dated Jun. 25, 2019.

* cited by examiner

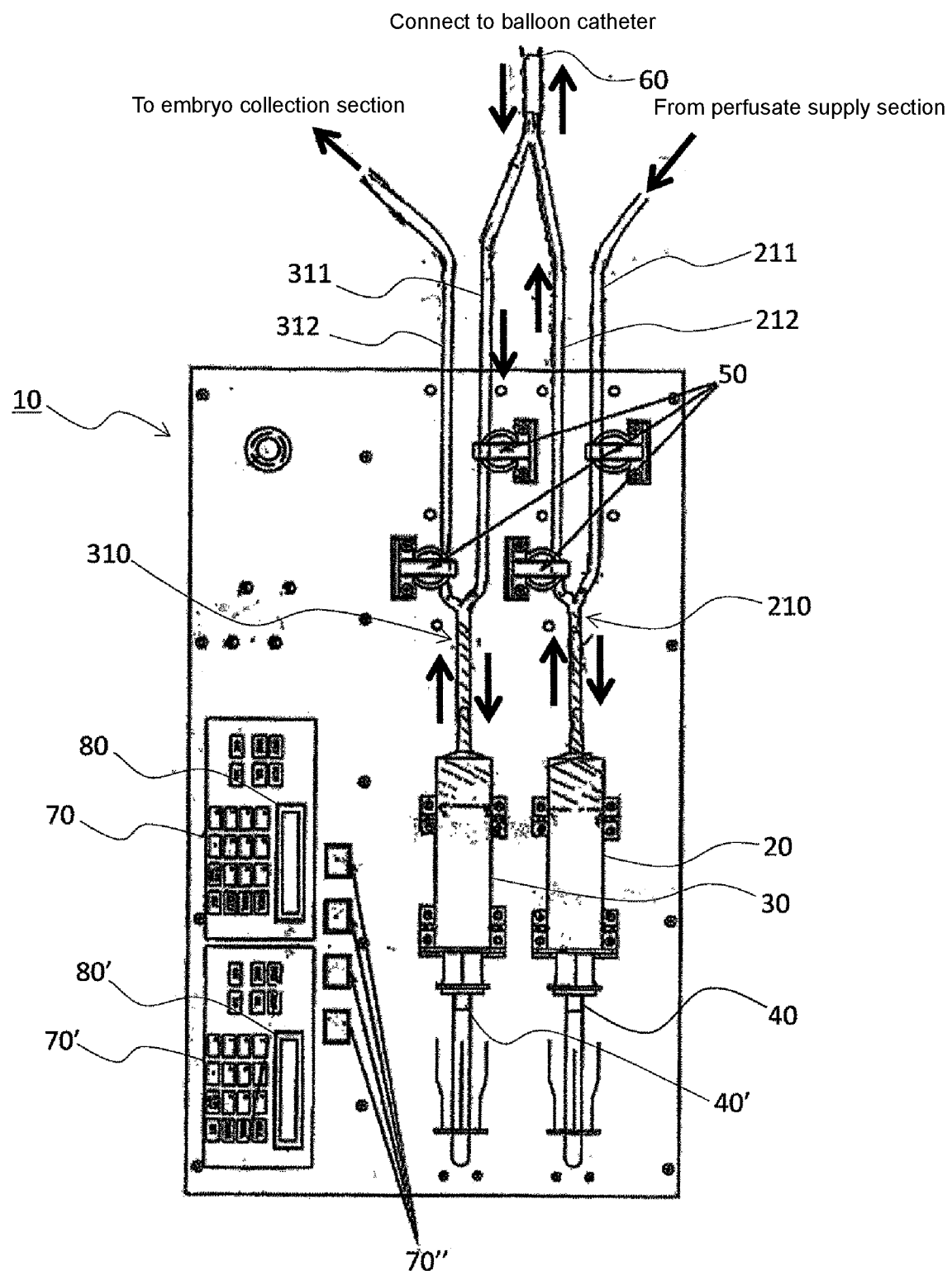

LIVESTOCK FERTILIZED-EGG RECOVERY DEVICE

TECHNICAL FIELD

The present invention relates to a livestock embryo collection apparatus, a method of controlling the apparatus, a program for carrying out the control method, and a method of collecting an embryo(s) in a livestock uterus.

BACKGROUND ART

In recent years, in spite of the shrinking production base in animal and dairy husbandry, the number of cases of transfer of Japanese Black Cattle embryos using dairy cows as surrogate mothers is increasing from the viewpoint of improvement of the producers' income and the like.

However, according to the Act on Improvement and Increased Production of Livestock and the Veterinarian Act of Japan, collection of embryos from the uterus of a living cattle is allowed only for veterinarians who passed the national examination. Moreover, at present, there are only a small number of veterinarians for industrial animals, and the number of technicians for collection of bovine embryos is also insufficient. Furthermore, techniques related to nonsurgical collection of embryos from the uterus of a living cattle are highly difficult since these techniques require certain levels of experience and skill. Mainly because of such a background, embryo production does not increase, and production of embryos by in vivo fertilization remains not enough to meet the demand.

A common method of collecting embryos from the uterus of a living cattle is the method called intrauterine circulatory perfusion method (Non-Patent Document 1), wherein a balloon catheter is inserted and fixed in a uterine horn, and then a perfusate is injected into the uterine horn, followed by recovering the perfusate together with embryos. As labor-saving simple apparatuses for collecting embryos from the bovine uterus by the intrauterine circulatory perfusion method, apparatuses utilizing a battery-powered air pump for injection of the perfusate have been reported (Non-Patent Documents 2 and 3). These reports suggest that, with these apparatuses, the injection rate of the perfusate can be increased compared to the gravity flow method utilizing the atmospheric pressure, so that the working time for the collection can be reduced.

PRIOR ART DOCUMENTS

Non-Patent Document(s)

Non-Patent Document 1: "Bovine Embryo Transfer", written and edited by Hiroshi Kanagawa. Kindai Shuppan Co., Ltd., Mar. 10, 1984. pp. 38-52.
Non-Patent Document 2: Study of Embryo Collection Method Using "Anywhere Perfusion Apparatus". Yotaro Komatsu et al. (home page of the website of Nagano Prefecture>Ina Livestock Hygiene Service Center>Investigation and Research>Investigation (2002), full text, https://www.pref.nagano.lg.jp/inakachiku/chosa/documents/2002komatsu-paper.pdf).
Non-Patent Document 3: Establishment of Simplified Technique for Embryo Transfer (Development of Simple Embryo Collection Technique). Yoshiyuki Fukumi and Susumu Tachikawa. Bulletin of Tokushima Prefectural Agriculture, Forestry and Fisheries Technology Center Livestock Research Institute, (3) 2003. 12. pp. 27-30.

SUMMARY OF THE INVENTION

Problems to be Solved by the Invention

An object of the present invention is to provide means that enables collection of embryos from the uterus of a living livestock animal, especially cattle, easily in a short time with the same accuracy as that achieved by a skilled technician.

Means for Solving the Problems

As a result of intensive study, the present inventors completed the following inventions.
  [1] A livestock embryo collection apparatus comprising:
    a syringe I for sucking a perfusate from a perfusate supply section and injecting the perfusate into a livestock uterus;
    a liquid transfer line I which is connected to the syringe I and bifurcated, comprising: a liquid transfer line section I-i for connection to the perfusate supply section; and a liquid transfer line section I-ii for connection to a balloon catheter;
    a syringe II for collecting the perfusate injected into the livestock uterus and discharging the perfusate into an embryo collection section;
    a liquid transfer line II which is connected to the syringe II and bifurcated, comprising: a liquid transfer line section II-i for connection to the balloon catheter; and a liquid transfer line section II-ii for connection to the embryo collection section;
    a liquid transfer direction control section for controlling the direction of transfer of the perfusate in the liquid transfer lines;
    a syringe pump control section for controlling pump operation of the syringe I and the syringe II; and
    an input section for a user to input an instruction;
    wherein the liquid transfer line section I-ii and the liquid transfer line section II-i join together to provide a balloon catheter connection section at the tip thereof.
  [2] The apparatus according to [1], wherein the syringe pump control section carries out an operation of sucking the perfusate from the perfusate supply section by the syringe I and an operation of collecting the perfusate from the livestock uterus by the syringe II in parallel, and carries out an operation of injecting the perfusate into the livestock uterus by the syringe I and an operation of discharging the collected perfusate into the embryo collection section by the syringe II in parallel.
  [3] The apparatus according to claim 1 or 2, wherein the livestock is a large mammal.
  [4] The apparatus according to [1] or [2], wherein the livestock is cattle.
  [5] The apparatus according to any one of [1] to [4], wherein the liquid transfer direction control section comprises: a shut-off valve provided for each of the liquid transfer line section I-i, liquid transfer line section I-ii, liquid transfer line section II-i, and liquid transfer line section II-ii; and a valve control section for controlling opening and closing of the shut-off valves.
  [6] The apparatus according to any one of [1] to [4], wherein the liquid transfer direction control section comprises: a three-way stopcock I and a three-way stopcock II provided for the branched portion of the liquid transfer line I and the branched portion of the liquid transfer line II, respectively; and a three-way stopcock control section for controlling the direction of each three-way stopcock.

[7] The apparatus according to any one of [1] to [4], wherein the liquid transfer direction control section comprises a check valve provided for each of the liquid transfer line section I-i, liquid transfer line section I-ii, liquid transfer line section II-i, and liquid transfer line section II-ii.

[8] A method of controlling the livestock embryo collection apparatus according to [5], the method comprising:

Step A of carrying out a sucking operation of the syringe I without operating the syringe II, in a state where: the shut-off valve for the liquid transfer line section I-i is opened; and the shut-off valve for the liquid transfer line section I-ii is closed;

Step B of carrying out a discharging operation of the syringe I without operating the syringe II, in a state where: the shut-off valve for the liquid transfer line section I-i is closed; and the shut-off valve for the liquid transfer line section I-ii is opened;

Step C of carrying out a sucking operation of the syringe I and a sucking operation of the syringe II in parallel, in a state where: the shut-off valve for the liquid transfer line section I-i is opened; the shut-off valve for the liquid transfer line section I-ii is closed; the shut-off valve for the liquid transfer line section II-i is opened; and the shut-off valve for the liquid transfer line section II-ii is closed;

Step D of carrying out a discharging operation of the syringe I and a discharging operation of the syringe II in parallel, in a state where: the shut-off valve for the liquid transfer line section I-i is closed; the shut-off valve for the liquid transfer line section I-ii is opened; the shut-off valve for the liquid transfer line section II-i is closed; and the shut-off valve for the liquid transfer line section II-ii is opened;

Step E of carrying out Step C and Step D again, which Step E is carried out once, twice or more times;

Step F of carrying out a sucking operation of the syringe II without operating the syringe I, in a state where: the shut-off valve for the liquid transfer line section II-i is opened; and the shut-off valve for the liquid transfer line section II-ii is closed; and Step G of carrying out a discharging operation of the syringe II without operating the syringe I, in a state where: the shut-off valve for the liquid transfer line section II-i is closed; and the shut-off valve for the liquid transfer line section II-ii is opened.

[9] A method of controlling the livestock embryo collection apparatus according to [6], the method comprising:

Step A' of carrying out a sucking operation of the syringe I without operating the syringe II, in a state where the three-way stopcock I allows liquid transfer between the syringe I and the liquid transfer line section I-i, and blocks liquid transfer between the syringe I and the liquid transfer line section I-ii;

Step B' of carrying out a discharging operation of the syringe I without operating the syringe II, in a state where the three-way stopcock I blocks liquid transfer between the syringe I and the liquid transfer line section I-i, and allows liquid transfer between the syringe I and the liquid transfer line section I-ii;

Step C' of carrying out a sucking operation of the syringe I and a sucking operation of the syringe II in parallel, in a state where the three-way stopcock I allows liquid transfer between the syringe I and the liquid transfer line section I-i, and blocks liquid transfer between the syringe I and the liquid transfer line section I-ii, and where the three-way stopcock II allows liquid transfer between the syringe II and the liquid transfer line section II-i, and blocks liquid transfer between the syringe II and the liquid transfer line section II-ii;

Step D' of carrying out a discharging operation of the syringe I and a discharging operation of the syringe II in parallel, in a state where the three-way stopcock I blocks liquid transfer between the syringe I and the liquid transfer line section I-i, and allows liquid transfer between the syringe I and the liquid transfer line section I-ii, and where the three-way stopcock II blocks liquid transfer between the syringe II and the liquid transfer line section II-i, and allows liquid transfer between the syringe II and the liquid transfer line section II-ii;

Step E' of carrying out Step C' and Step D' again, which Step E' is carried out once, twice or more times;

Step F' of carrying out a sucking operation of the syringe II without operating the syringe I, in a state where the three-way stopcock II allows liquid transfer between the syringe II and the liquid transfer line section II-i, and blocks liquid transfer between the syringe II and the liquid transfer line section II-ii; and Step G' of carrying out a discharging operation of the syringe II without operating the syringe I, in a state where the three-way stopcock II blocks liquid transfer between the syringe II and the liquid transfer line section II-i, and allows liquid transfer between the syringe II and the liquid transfer line section II-ii.

[10] A method of controlling the livestock embryo collection apparatus according to [7], the method comprising:

Step A" of carrying out a sucking operation of the syringe I without operating the syringe II;

Step B" of carrying out a discharging operation of the syringe I without operating the syringe II;

Step C" of carrying out a sucking operation of the syringe I and a sucking operation of the syringe II in parallel;

Step D" of carrying out a discharging operation of the syringe I and a discharging operation of the syringe II in parallel;

Step E" of carrying out Step C" and Step D" again, which Step E" is carried out once, twice or more times;

Step F" of carrying out a sucking operation of the syringe II without operating the syringe I; and Step G" of carrying out a discharging operation of the syringe II without operating the syringe I.

[11] The method according to any one of [8] to [10], wherein Step E, E', or E" is carried out twice or more times.

[12] The method according to [11], wherein the volumes of liquid sucked and discharged by the syringes are selected from the following Setting 1 to Setting 4 according to an instruction from a user to carry out each step:

<Setting 1>
  (1) in Step A, A', or A", the syringe I sucks 25 ml±5 ml of perfusate;
  (2) in Step B, B', or B", the syringe I discharges 25 ml±5 ml of perfusate;
  (3) in Step C, C', or C", the syringe I sucks 30 ml±5 ml of perfusate, and the syringe II sucks 25 ml±5 ml of perfusate;
  (4) in Step D, D', or D", the syringe I discharges 30 ml±5 ml of perfusate, and the syringe II discharges 25 ml±5 ml of perfusate;
  (5) in Step E, E', or E",
    (5-1) the syringe I sucks 35 ml±5 ml of perfusate, and the syringe II sucks 30 ml±5 ml of perfusate;
    (5-2) the syringe I discharges 35 ml±5 ml of perfusate, and the syringe II discharges 30 ml±5 ml of perfusate;
    (5-3) the syringe I sucks 40 ml±5 ml of perfusate, and the syringe II sucks 35 ml±5 ml of perfusate;
    (5-4) the syringe I discharges 40 ml±5 ml of perfusate, and the syringe II discharges 35 ml±5 ml of perfusate;
    (5-5) the syringe I sucks 42.5 ml±5 ml of perfusate, and the syringe II sucks 40 ml±5 ml of perfusate;
    (5-6) the syringe I discharges 42.5 ml±5 ml of perfusate, and the syringe II discharges 40 ml±5 ml of perfusate;
    (5-7) the syringe I sucks 45 ml±5 ml of perfusate, and the syringe II sucks 42.5 ml±5 ml of perfusate;
    (5-8) the syringe I discharges 45 ml±5 ml of perfusate, and the syringe II discharges 42.5 ml±5 ml of perfusate;
    (5-9) the syringe I sucks 47.5 ml±5 ml of perfusate, and the syringe II sucks 45 ml±5 ml of perfusate;
    (5-10) the syringe I discharges 47.5 ml±5 ml of perfusate, and the syringe II discharges 45 ml±5 ml of perfusate;
    (5-11) the syringe I sucks 50 ml±5 ml of perfusate, and the syringe II sucks 47.5 ml±5 ml of perfusate;
    (5-12) the syringe I discharges 50 ml±5 ml of perfusate, and the syringe II discharges 47.5 ml±5 ml of perfusate;
  (6) in Step F, F', or F", the syringe II sucks 50 ml±5 ml of perfusate;
  (7) in Step G, G', or G", the syringe II discharges 50 ml±5 ml of perfusate;
<Setting 2>
  (1) in Step A, A', or A", the syringe I sucks 35 ml±5 ml of perfusate;
  (2) in Step B, B', or B", the syringe I discharges 35 ml±5 ml of perfusate;
  (3) in Step C, C', or C", the syringe I sucks 40 ml±5 ml of perfusate, and the syringe II sucks 35 ml±5 ml of perfusate;
  (4) in Step D, D', or D", the syringe I discharges 40 ml±5 ml of perfusate, and the syringe II discharges 35 ml±5 ml of perfusate;
  (5) in Step E, E', or E",
    (5-1) the syringe I sucks 45 ml±5 ml of perfusate, and the syringe II sucks 40 ml±5 ml of perfusate;
    (5-2) the syringe I discharges 45 ml±5 ml of perfusate, and the syringe II discharges 40 ml±5 ml of perfusate;
    (5-3) the syringe I sucks 50 ml±5 ml of perfusate, and the syringe II sucks 45 ml±5 ml of perfusate;
    (5-4) the syringe I discharges 50 ml±5 ml of perfusate, and the syringe II discharges 45 ml±5 ml of perfusate;
    (5-5) the syringe I sucks 52.5 ml±5 ml of perfusate, and the syringe II sucks 50 ml±5 ml of perfusate;
    (5-6) the syringe I discharges 52.5 ml±5 ml of perfusate, and the syringe II discharges 50 ml±5 ml of perfusate;
    (5-7) the syringe I sucks 55 ml±5 ml of perfusate, and the syringe II sucks 52.5 ml±5 ml of perfusate;
    (5-8) the syringe I discharges 55 ml±5 ml of perfusate, and the syringe II discharges 52.5 ml±5 ml of perfusate;
    (5-9) the syringe I sucks 57.5 ml±5 ml of perfusate, and the syringe II sucks 55 ml±5 ml of perfusate;
    (5-10) the syringe I discharges 57.5 ml±5 ml of perfusate, and the syringe II discharges 55 ml±5 ml of perfusate;
    (5-11) the syringe I sucks 60 ml±5 ml of perfusate, and the syringe II sucks 57.5 ml±5 ml of perfusate;
    (5-12) the syringe I discharges 60 ml±5 ml of perfusate, and the syringe II discharges 57.5 ml±5 ml od perfusate;
  (6) in Step F, F', or F", the syringe II sucks 60 ml±5 ml of perfusate;
  (7) in Step G, G', or G", the syringe II discharges 60 ml±5 ml of perfusate;
<Setting 3>
  (1) in Step A, A', or A", the syringe I sucks 45 ml±5 ml of perfusate;
  (2) in Step B, B', or B", the syringe I discharges 45 ml±5 ml of perfusate;
  (3) in Step C, C', or C", the syringe I sucks 50 ml±5 ml of perfusate, and the syringe II sucks 45 ml±5 ml of perfusate;
  (4) in Step D, D', or D", the syringe I discharges 50 ml±5 ml of perfusate, and the syringe II discharges 45 ml±5 ml of perfusate;
  (5) in Step E, E', or E",
    (5-1) the syringe I sucks 55 ml±5 ml of perfusate, and the syringe II sucks 50 ml±5 ml of perfusate;
    (5-2) the syringe I discharges 55 ml±5 ml of perfusate, and the syringe II discharges 50 ml±5 ml of perfusate;
    (5-3) the syringe I sucks 60 ml±5 ml of perfusate, and the syringe II sucks 55 ml±5 ml of perfusate;
    (5-4) the syringe I discharges 60 ml±5 ml of perfusate, and the syringe II discharges 55 ml±5 ml of perfusate;
    (5-5) the syringe I sucks 62.5 ml±5 ml of perfusate, and the syringe II sucks 60 ml±5 ml of perfusate;
    (5-6) the syringe I discharges 62.5 ml±5 ml of perfusate, and the syringe II discharges 60 ml±5 ml of perfusate;
    (5-7) the syringe I sucks 65 ml±5 ml of perfusate, and the syringe II sucks 62.5 ml±5 ml of perfusate;
    (5-8) the syringe I discharges 65 ml±5 ml of perfusate, and the syringe II discharges 62.5 ml±5 ml of perfusate
    (5-9) the syringe I sucks 67.5 ml±5 ml of perfusate, and the syringe II sucks 65 ml±5 ml of perfusate;
    (5-10) the syringe I discharges 67.5 ml±5 ml of perfusate, and the syringe II discharges 65 ml±5 ml of perfusate;
    (5-11) the syringe I sucks 70 ml±5 ml of perfusate, and the syringe II sucks 67.5 ml±5 ml of perfusate;

(5-12) the syringe I discharges 70 ml±5 ml of perfusate, and the syringe II discharges 67.5 ml±5 ml of perfusate;
(6) in Step F, F', or F", the syringe II sucks 70 ml±5 ml of perfusate;
(7) in Step G, G', or G", the syringe II discharges 70 ml±5 ml of perfusate;

<Setting 4>
(1) in Step A, A', or A", the syringe I sucks 55 ml±5 ml of perfusate;
(2) in Step B, B', or B", the syringe I discharges 55 ml±5 ml of perfusate;
(3) in Step C, C', or C", the syringe I sucks 60 ml±5 ml of perfusate, and the syringe II sucks 55 ml±5 ml of perfusate;
(4) in Step D, D', or D", the syringe I discharges 60 ml±5 ml of perfusate, and the syringe II discharges 55 ml±5 ml of perfusate;
(5) in Step E, E', or E",
  (5-1) the syringe I sucks 65 ml±5 ml of perfusate, and the syringe II sucks 60 ml±5 ml of perfusate;
  (5-2) the syringe I discharges 65 ml±5 ml of perfusate, and the syringe II discharges 60 ml±5 ml of perfusate;
  (5-3) the syringe I sucks 70 ml±5 ml of perfusate, and the syringe II sucks 65 ml±5 ml of perfusate;
  (5-4) the syringe I discharges 70 ml±5 ml of perfusate, and the syringe II discharges 65 ml±5 ml of perfusate;
  (5-5) the syringe I sucks 72.5 ml±5 ml of perfusate, and the syringe II sucks 70 ml±5 ml of perfusate;
  (5-6) the syringe I discharges 72.5 ml±5 ml of perfusate, and the syringe II discharges 70 ml±5 ml of perfusate;
  (5-7) the syringe I sucks 75 ml±5 ml of perfusate, and the syringe II sucks 72.5 ml±5 ml of perfusate;
  (5-8) the syringe I discharges 75 ml±5 ml of perfusate, and the syringe II discharges 72.5 ml±5 ml of perfusate;
  (5-9) the syringe I sucks 77.5 ml±5 ml of perfusate, and the syringe II sucks 75 ml±5 ml of perfusate;
  (5-10) the syringe I discharges 77.5 ml±5 ml of perfusate, and the syringe II discharges 75 ml±5 ml of perfusate;
  (5-11) the syringe I sucks 80 ml±5 ml of perfusate, and the syringe II sucks 77.5 ml±5 ml of perfusate;
  (5-12) the syringe I discharges 80 ml±5 ml of perfusate, and the syringe II discharges 77.5 ml±5 ml of perfusate;
(6) in Step F, F', or F", the syringe II sucks 80 ml±5 ml of perfusate;
(7) in Step G, G', or G", the syringe II discharges 80 ml±5 ml of perfusate.

[13] A program which causes a computer of the livestock embryo collection apparatus to carry out each step of the method of controlling the apparatus according to any one of [8] to [12].

[14] A method of collecting an embryo(s) in a livestock uterus, the method comprising:
Step 1 of bringing the apparatus according to any one of claims 1 to 7 into a state where: a balloon catheter inserted into a livestock uterus is connected to the balloon catheter connection section; the tip of the liquid transfer line section I-i is connected to the perfusate supply section; and the tip of the liquid transfer line section II-ii is connected to the embryo collection section;
Step 2 of sucking the perfusate from the perfusate supply section into the syringe I, in a state where the flow of the perfusate from the livestock uterus toward the syringe I is prevented;
Step 3 of injecting the perfusate from the syringe I into the livestock uterus through the balloon catheter, in a state where the flow of the perfusate from the syringe I toward the perfusate supply section is prevented;
Step 4 of sucking the perfusate into the syringe I in a state where the flow of the perfusate from the livestock uterus toward the syringe I is prevented, and, in parallel, collecting the perfusate in the livestock uterus with the syringe II through the balloon catheter in a state where the flow of the perfusate from the embryo collection section toward the syringe II is prevented;
Step 5 of injecting the perfusate from the syringe I into the livestock uterus through the balloon catheter in a state where the flow of the perfusate from the syringe I toward the perfusate supply section is prevented, and, in parallel, discharging the collected perfusate in the syringe II into the embryo collection section, in a state where the flow of the perfusate from the syringe II toward the livestock uterus is prevented;
Step 6 of further carrying out Step 4 and Step 5 at least once;
Step 7 of collecting the perfusate in the livestock uterus with the syringe II through the balloon catheter, in a state where the flow of the perfusate from the embryo collection section toward the syringe II is prevented; and
Step 8 of discharging the perfusate collected in the syringe II into the embryo collection section, in a state where the flow of the perfusate from the syringe II toward the livestock uterus is prevented.

Effect of the Invention

According to the apparatus of the present invention, an operation of sucking the perfusate from the perfusate supply section by the syringe I and an operation of collecting the perfusate from the livestock uterus by the syringe II are carried out in parallel, and an operation of injecting the perfusate into the livestock uterus by the syringe I and an operation of discharging the collected perfusate into the embryo collection section by the syringe II are carried out in parallel. By this, injection and removal of the perfusate can be carried out with a high speed, and therefore the working time for collection of embryos from the uterus of a living livestock animal can be largely reduced. The user only needs to have a technique for inserting a balloon catheter into a uterine horn and fixing the balloon catheter therein, and just by selecting the liquid volumes sucked and discharged by the syringes suitable for the size of the livestock uterus, the user can collect embryos from the uterus of a living livestock animal easily, quickly, and with the same accuracy as that achieved by a skilled technician.

BRIEF DESCRIPTION OF THE DRAWINGS

FIG. 1 is a diagram illustrating the configuration of an embryo collection apparatus of the present invention according to the first mode, which employs shut-off valves as the liquid transfer direction control section.

MODE FOR CARRYING OUT THE INVENTION

The livestock animal to which the present invention is applied is generally a large mammal, typically cattle. However, the present invention is applicable also to other livestock animals such as a pig. In the present description, the present invention is illustrated below mainly for collection of embryos from a bovine uterus. However, the illustration is not meant to exclude application of the invention to livestock animals other than cattle.

The configuration of the apparatus of the present invention is described based on a drawing. As described later, there are three modes of the apparatus of the present invention according to the difference in the liquid transfer direction control section. The example shown in FIG. 1 represents one of these modes.

An apparatus of the present invention 10 comprises two syringes. A syringe I 20 is a syringe for sucking a perfusate from a perfusate supply section, and injecting the perfusate into a livestock uterus. A syringe II 30 is a syringe for collecting the perfusate injected into the livestock uterus, and discharging the perfusate into an embryo collection section. The capacity of the syringe may be selected in accordance with the size of the uterus of the livestock animal from which the embryos are to be collected. A capacity of 100 ml is usually sufficient.

The liquid transfer line for transferring the perfusate comprises a liquid transfer line I 210 connected to the syringe I 20, and a liquid transfer line II 310 connected to the syringe II 30. The liquid transfer line I 210 is bifurcated to constitute a liquid transfer line section I-i 211 and a liquid transfer line section I-ii 212. The liquid transfer line II 310 is also bifurcated to constitute a liquid transfer line section II-i 311 and a liquid transfer line section II-ii 312. The liquid transfer line section I-i 211 is a line for connection to the perfusate supply section. The liquid transfer line section I-ii 212 and the liquid transfer line section II-i 311 join together to provide a balloon catheter connection section 60 at the tip thereof. The liquid transfer line section II-ii 312 is a line for connection to the embryo collection section. Each black arrow drawn along each liquid transfer line indicates the direction of transfer of the perfusate.

The liquid transfer line may be constituted by connecting tubes made of a flexible resin such as a silicone resin or vinyl chloride resin together through three-way connecting members (Y-shaped connectors). It is preferred to provide a line-holding section which detachably holds the liquid transfer line on the apparatus, to enable washing and reuse, or disposal, of the liquid transfer line.

The perfusate supply section is connected to the tip of the liquid transfer line section I-i 211 upon the use of the apparatus. The perfusate supply section includes a container such as a plastic bag or bottle containing a perfusate enclosed therein. The perfusate may be the same as a perfusate conventionally used in collecting bovine embryos by the intrauterine perfusion method. Specific examples of the perfusate include solutions prepared by adding an appropriate amount of inactivated serum, bovine serum albumin preparation or the like to physiological saline, Ringer solution, commonly used drip infusion preparations. Eagle's MEM, Dulbecco's PBS, etc.

To the balloon catheter connection section 60, a main tube of the balloon catheter is connected upon the use of the apparatus. The structure of the connection section is not limited as long as the connection can be achieved detachably and liquid-tightly. Since the connection portion in the main-tube side of the balloon catheter usually has a female-side structure, a connecting member having a male-side structure to be inserted into this female-side structure may be arranged at the tip of the joined liquid transfer line, to provide the balloon catheter connection section.

The balloon catheter connected to the apparatus of the present invention is not limited, and may be a balloon catheter conventionally used for collection of livestock embryos. In cases where embryos are collected from the uterus of cattle, a balloon catheter for cattle may be used. In cases where embryos are collected from the uterus of a pig, a balloon catheter for pigs may be used.

The embryo collection section is connected to the tip of the liquid transfer line section II-ii 312 upon the use of the apparatus. The embryo collection section may comprise a filter for separating and collecting embryos from the perfusate collected from the livestock uterus, and may also comprise, as desired, a container for receiving waste perfusate. The filter may be a filter conventionally used for the intrauterine circulatory perfusion method.

The liquid transfer direction control section 50 controls how to transfer the perfusate within the liquid transfer line. By the liquid transfer direction control section 50, the flow of the perfusate from the syringe I 20 toward the perfusate supply section is prevented in the liquid transfer line section I-i 211; the flow of the perfusate from the livestock uterus to the syringe I 20 is prevented in the liquid transfer line section I-ii 212; the flow of the perfusate from the syringe II 30 toward the livestock uterus is prevented in the liquid transfer line section II-i 311; and the flow of the perfusate from the embryo collection section toward the syringe II 30 is prevented in the liquid transfer line section II-ii 312. Modes of the liquid transfer direction control section 50 include the following three modes.

In the first mode, the liquid transfer direction control section 50 comprises: a shut-off valve provided for each of the liquid transfer line section I-i 211, the liquid transfer line section I-ii 212, liquid transfer line section II-i 311, and the liquid transfer line section II-ii 312; and a valve control section for controlling opening and closing of the shut-off valves. The apparatus 10 of the present invention exemplified in FIG. 1 is an example of the first mode. Specific examples of the shut-off valve include a pinch valve, a two-way stopcock, and the like. In the case of a pinch valve, the valve control section controls the operation of the pinch valve to close the liquid transfer line by pinching, and the operation of opening of the pinch valve. In the case of a two-way stopcock, the valve control section controls the operation of switching the lever of the stopcock between the closed position and the open position.

In the second mode, the liquid transfer direction control section 50 comprises: a three-way stopcock I and a three-way stopcock II provided for the branched portion of the liquid transfer line I 210 and the branched portion of the liquid transfer line II 310, respectively; and a three-way stopcock control section for controlling the direction of the three-way stopcocks. The three-way stopcock control section controls the operation of switching the lever position of the stopcock. The three-way stopcock I is controlled by the three-way stopcock control section to perform the operation of switching between the state where liquid transfer is allowed between the syringe I 20 and the liquid transfer line section I-i 211 and blocked between the syringe I 20 and the liquid transfer line section I-ii 212, and the state where liquid transfer is blocked between the syringe I 20 and the liquid transfer line section I-i 211 and is allowed between the syringe I 20 and the liquid transfer line section I-ii 212. The three-way stopcock II is controlled by the three-way stopcock control section to perform the operation of switching between the state where liquid transfer is allowed between the syringe II 30 and the liquid transfer line section II-i 311 and blocked between the syringe II 30 and the liquid transfer line section II-ii 312, and the state where liquid transfer is blocked between the syringe II 30 and the liquid transfer line section II-i 311 and allowed between the syringe II 30 and the liquid transfer line section II-ii 312.

In the third mode, the liquid transfer direction control section 50 comprises a check valve provided for each of the liquid transfer line section I-i 211, liquid transfer line section I-li 212, liquid transfer line section II-i 311, and liquid transfer line section II-ii 312. The direction of the check valve may be set such that the perfusate flows in the following direction: perfusate supply section→syringe I→balloon catheter (in the livestock uterus)→syringe II→embryo collection section.

A syringe pump control section 40, 40' controls pump operation of the syringe I 20 and the syringe II 30. The syringe pump control section 40, 40' comprises a syringe inner-cylinder holding section capable of reciprocating along a straight line. The outer cylinders of the two syringes are held and fixed to be immovable on the apparatus, and each inner cylinder is held by the inner-cylinder holding section. The reciprocating movement of the inner-cylinder holding section is parallel to the direction of the syringe outer cylinder, and each inner cylinder moves in the sucking direction or discharging direction by the movement of the inner-cylinder holding section. Preferably, the two syringes are detachably fixed or held on the apparatus, to enable washing and reuse, or disposal, of the syringes.

The liquid transfer rate of the perfusate depends on the moving rate of the syringe inner cylinders by the syringe pump control section 40, 40'. The liquid transfer rate may be about 500 to 1500 ml/minute, preferably about 700 to 1000 ml/minute.

The syringe pump control section 40, 40' carry out an operation of sucking the perfusate into the syringe I 20 and the syringe II 30 in parallel, and also carry out an operation of discharging the perfusate from the syringe I 20 and the syringe II 30 in parallel (at the same time). The operation of sucking the perfusate into the syringe I 20 is an operation of sucking the perfusate from the perfusate supply section. The operation of discharging the perfusate from the syringe I 20 is an operation of injecting the perfusate into the livestock uterus. The operation of sucking the perfusate into the syringe II 30 is an operation of collecting the perfusate from the livestock uterus. The operation of discharging the perfusate from the syringe II 30 is an operation of discharging the perfusate collected from the livestock uterus into the embryo collection section. Thus, the syringe pump control section 40, 40' carries out: an operation of sucking the perfusate from the perfusate supply section by the syringe I 20 and an operation of collecting the perfusate from the livestock uterus by the syringe II 30 in parallel, and carries out an operation of injecting the perfusate into the livestock uterus by the syringe I 20 and an operation of discharging the collected perfusate into the embryo collection section by the syringe II 30 in parallel. There may be a slight time lag (of not more than about 1 to 3 seconds) between the start of the operation of the syringe I 20 and the start of the operation of the syringe II 30.

The control of the sucking/discharging operation (pump operation) by the syringe pump control section 40, 40' and the control of the liquid transfer direction by the liquid transfer direction control section 50 are carried out in a coordinated manner, by which it becomes possible to carry out the suction of the perfusate from the perfusate supply section by the syringe I 20 and the collection of the perfusate from the livestock uterus by the syringe II 30 in parallel, and to carry out the injection of the perfusate into the livestock uterus by the syringe I 20 and the discharge of the perfusate into the embryo collection section by the syringe II 30 in parallel. In the case of the third mode described above, the direction of liquid transfer is set in a fixed direction by the check valve. Thus, the sucking operation by the two syringes can be carried out in parallel, and the discharging operation by the two syringes can also be carried out in parallel, only by controlling the pump operation by the syringe pump control section 40, 40', without the coordinated operation of the syringe pump control section 40, 40' and the liquid transfer direction control section 50.

The input section 70, 70', 70" is a constitution for inputting instructions by the user, and may comprises a touch panel, button, switch, or the like. In the case of FIG. 1, sheet switches (70, 70') and buttons (70") are provided as the input section. The input section 70 is a sheet switch for inputting information/instruction related to the pump operation of the syringe I 20, and the input section 70' is a sheet switch for inputting information/instruction related to the pump operation of the syringe II 30.

The apparatus of the present invention may be configured such that the initial volume of the liquid (initial liquid volume) sucked into the syringe, the number of times of perfusion, the degree of increase in the liquid volume per perfusion operation, and/or the like can be input or selected by the user using the input section. For example, the apparatus may be configured to allow input to set the initial liquid volume to 20 ml, the degree of increase in the liquid volume to +3 ml, and the number of times of perfusion to 5, such that the liquid volume in the first suction-discharge by the syringe I and the syringe II is 20 ml, and such that the operation is completed after five times of perfusion in which the volume of the liquid sucked/discharged is increased by 3 ml each time (wherein one perfusion is defined as the operation of sucking a certain volume of perfusate and discharging it into the uterus by the syringe I and then collecting the perfusate from the uterus and discharging it by the syringe II). Or, the apparatus may be configured such that several or more patterns of the volume of liquid sucked/discharged in accordance with the size of the livestock uterus are preliminarily stored in the apparatus, and such that the user can select an appropriate pattern therefrom. In the example of the apparatus shown in FIG. 1, the apparatus is configured such that four patterns are stored in the apparatus, and such that the user selects one of the patterns using four buttons 70". Preferred examples of the pattern setting for the volume of liquid sucked/discharged in accordance with the size of a bovine uterus are described later.

The apparatus of the present invention may comprise a display section 80, 80' such as liquid crystal panels which display the operating status of the syringe I 20 and the syringe II 30 (for example, whether each syringe is in a sucking state or discharging state, how much liquid is present within the syringes, etc.). In cases where the input section is a touch panel, the touch panel can function also as a display section. In the example of FIG. 1, the operating status of the syringe I 20 is displayed on the display section 80, and the operating state of the syringe II 30 is displayed on the display section 80'.

Each step of the method of controlling the apparatus for collection of a livestock embryo(s) of the present invention is described below for each of the three modes described above.

In the first mode, the apparatus employs shut-off valves as the liquid transfer direction control section, and the control method comprises the following Steps A to G in this order.

(Step A) A sucking operation of the syringe I 20 is carried out without operating the syringe II 30, in a state where: the shut-off valve for the liquid transfer line section I-i 211 is opened; and the shut-off valve for the liquid transfer line section I-ii 212 is closed.

(Step B) A discharging operation of the syringe I 20 is carried out without operating the syringe II 30, in a state where: the shut-off valve for the liquid transfer line section I-i 211 is closed; and the shut-off valve for the liquid transfer line section I-ii 212 is opened.

(Step C) A sucking operation of the syringe I 20 and a sucking operation of the syringe II 30 are carried out in parallel, in a state where: the shut-off valve for the liquid transfer line section I-i 211 is opened; the shut-off valve for the liquid transfer line section I-ii 212 is closed; the shut-off valve for the liquid transfer line section II-i 311 is opened; and the shut-off valve for the liquid transfer line section II-ii 312 is closed.

(Step D) A discharging operation of the syringe I 20 and a discharging operation of the syringe II 30 are carried out in parallel, in a state where: the shut-off valve for the liquid transfer line section I-i 211 is closed; the shut-off valve for the liquid transfer line section I-ii 212 is opened; the shut-off valve for the liquid transfer line section II-i 311 is closed; and the shut-off valve for the liquid transfer line section II-ii 312 is opened.

(Step E) Step C and Step D are carried out again. Step F is carried out once, twice or more times.

(Step F) A sucking operation of the syringe II 30 is carried out without operating the syringe I 20, in a state where: the shut-off valve for the liquid transfer line section II-i 311 is opened; and the shut-off valve for the liquid transfer line section II-ii 312 is closed.

(Step G) A discharging operation of the syringe II 30 is carried out without operating the syringe I 20, in a state where: the shut-off valve for the liquid transfer line section II-i 311 is closed; and the shut-off valve for the liquid transfer line section II-ii 312 is opened.

In Steps A and B, the syringe II 30 does not operate, and therefore the shut-off valves for the liquid transfer line section II-i 311 and the liquid transfer line section II-ii 312 can be either in a closed state or in an open state. In Steps F and G, the syringe I 20 does not operate, and therefore the shut-off valves for the liquid transfer line section I-i 211 and the liquid transfer line section I-ii 212 can be either in a closed state or in an open state.

In the second mode, the apparatus employs three-way stopcocks as the liquid transfer direction control section, and the control method comprises the following Steps A' to G' in this order. The Steps A' to G' correspond to the Steps A to G, respectively, in the control method of the first mode.

(Step A') A sucking operation of the syringe I 20 is carried out without operating the syringe II 30, in a state where the three-way stopcock I allows liquid transfer between the syringe I 20 and the liquid transfer line section I-i 211, and blocks liquid transfer between the syringe I 20 and the liquid transfer line section I-ii 212.

(Step B') A discharging operation of the syringe I 20 is carried out without operating the syringe II 30, in a state where the three-way stopcock I blocks liquid transfer between the syringe I 20 and the liquid transfer line section I-i 211, and allows liquid transfer between the syringe I 20 and the liquid transfer line section I-ii 212.

(Step C') A sucking operation of the syringe I 20 and a sucking operation of the syringe II 30 are carried out in parallel, in a state where the three-way stopcock I allows liquid transfer between the syringe I 20 and the liquid transfer line section I-i 211, and blocks liquid transfer between the syringe I 20 and the liquid transfer line section I-ii 212, and where the three-way stopcock II allows liquid transfer between the syringe II 30 and the liquid transfer line section II-i 311, and blocks liquid transfer between the syringe II 30 and the liquid transfer line section II-ii 312.

(Step D') A discharging operation of the syringe I 20 and a discharging operation of the syringe II 30 are carried out in parallel, in a state where the three-way stopcock I blocks liquid transfer between the syringe I 20 and the liquid transfer line section I-i 211, and allows liquid transfer between the syringe I 20 and the liquid transfer line section I-ii 212, and where the three-way stopcock II blocks liquid transfer between the syringe II 30 and the liquid transfer line section II-i 311, and allows liquid transfer between the syringe II 30 and the liquid transfer line section II-ii 312.

(Step E') Step C' and Step D' are carried out again. Step E' is carried out once, twice or more times.

(Step F') A sucking operation of the syringe II 30 is carried out without operating the syringe I 20, in a state where the three-way stopcock II allows liquid transfer between the syringe II 30 and the liquid transfer line section II-i 311, and blocks liquid transfer between the syringe II 30 and the liquid transfer line section II-ii 312.

(Step G') A discharging operation of the syringe II 30 is carried out without operating the syringe I 20, in a state where the three-way stopcock II blocks liquid transfer between the syringe II 30 and the liquid transfer line section II-i 311, and allows liquid transfer between the syringe II 30 and the liquid transfer line section II-ii 312.

In Steps A' and B', the syringe II 30 does not operate, and therefore the direction of the three-way stopcock II can be in any state; it can be in a state where the part between the syringe II and the liquid transfer line section II-i is opened while the other is blocked, or can be in a state where the part between the syringe II and the liquid transfer line section II-ii is opened while the other is blocked. Similarly, in Steps F' and G', the syringe I 20 does not operate, and therefore the direction of the three-way stopcock I can be in any state; it can be in a state where the part between the syringe I and the liquid transfer line section I-i is opened while the other is blocked, or can be in a state where the part between the syringe I and the liquid transfer line section I-ii is opened while the other is blocked.

In the third mode, the apparatus employs check valves as the liquid transfer direction control section, and the control method comprises the following Steps A" to G" in this order. The Steps A" to G" correspond to the Steps A to G, respectively, in the control method of the first mode, and to the Steps A' to G', respectively, in the control method of the second mode. In this mode, the liquid transfer direction control section does not carry out an operation such as opening or closing, and therefore the syringe pump control section operates not in a coordinated manner with the liquid transfer direction control section.

(Step A") A sucking operation of the syringe I 20 is carried out without operating the syringe II 30.

(Step B") A discharging operation of the syringe I 20 is carried out without operating the syringe II 30.

(Step C") A sucking operation of the syringe I 20 and a sucking operation of the syringe II 30 are carried out in parallel.

(Step D") A discharging operation of the syringe I 20 and a discharging operation of the syringe II 30 are carried out in parallel.

(Step E") Step C" and Step D" are carried out again. Step E" is carried out once, twice or more times.

(Step F") A sucking operation of the syringe II 30 is carried out without operating the syringe I 20.

(Step G') A discharging operation of the syringe II 30 is carried out without operating the syringe II 20.

When one perfusion operation is defined as sucking and injection of the perfusate by the syringe I and collection and discharging of the perfusate by the syringe II, the perfusion operation in the present invention is preferably carried out not less than 4 times. For example, the perfusion operation may be carried out about 4 to 10 times, 4 to 8 times, or 6 to 8 times. In case where Step E, E', or E" (Step C+D, Step C'+D', or Step C"+D") is carried out twice, the number of times of the perfusion operation is 4. Thus, in the method of controlling the apparatus of the present invention, Step E, E', or E" is preferably carried out twice or more times, for example, about twice to 8 times, twice to 6 times, or 4 to 6 times.

In cases where the livestock animal is cattle, the uterine size can be classified as small to extra-large as follows. In general, parous cattle of about seven years old or older corresponds to an "old parous cattle".

TABLE I

| | |
|---|---|
| Small uterine size | Nulliparous Japanese cattle (Japanese Black Cattle, Japanese Brown Cattle, Japanese Polled Cattle, and Japanese Shorthorn Cattle) and parous cattle of cattle breeds with a small physique (such as Jersey cattle and Tajima Cattle) |
| Medium uterine size | Parous Japanese cattle and Nulliparous Holstein cattle |
| Large uterine size | Parous old Japanese cattle with an enlarged uterus, and parous Holstein cattle |
| Extra-large uterine size | Parous old Holstein cattle with an enlarged uterus |

Accordingly, in the collection of bovine embryos using the apparatus of the present invention, preferred specific examples of the pattern of the volume of the liquid sucked/discharged by the syringes include the following four patterns, which are in accordance with the above-described four categories. The liquid volumes presented in the tables are most preferred examples, and may be changed within the range of ±5 ml. For example, the pattern may be set with liquid volumes different from those presented in each table by +2 ml.

TABLE 2

<Setting 1 (small uterine size; perfusion operation, 8 times)>

| Syringe I | Syringe II | |
|---|---|---|
| 25 ml Suction | | Step A, A', A" |
| 25 ml Discharge | | Step B, B', B" |
| 30 ml Suction | 25 ml Suction | Step C, C', C" |
| 30 ml Discharge | 25 ml Discharge | Step D, D', D" |
| 35 ml Suction | 30 ml Suction | Step E, E', E" (first) |
| 35 ml Discharge | 30 ml Discharge | |
| 40 ml Suction | 35 ml Suction | Step E, E', E" (second) |
| 40 ml Discharge | 35 ml Discharge | |
| 42.5 ml Suction | 40 ml Suction | Step E, E', E" (third) |
| 42.5 ml Discharge | 40 ml Discharge | |
| 45 ml Suction | 42.5 ml Suction | Step E, E', E" (fourth) |
| 45 ml Discharge | 42.5 ml Discharge | |
| 47.5 ml Suction | 45 ml Suction | Step E, E', E" (fifth) |
| 47.5 ml Discharge | 45 ml Discharge | |
| 50 ml Suction | 47.5 ml Suction | Step E, E', E" (sixth) |
| 50 ml Discharge | 47.5 ml Discharge | |
| | 50 ml Suction | Step F, F', F" |
| | 50 ml Discharge | Step G, G', G" |
| total 315 ml | total 315 ml | |

TABLE 3

<Setting 2 (medium uterine size; perfusion operation, 8 times)>

| Syringe I | Syringe II | |
|---|---|---|
| 35 ml Suction | | Step A, A', A" |
| 35 ml Discharge | | Step B, B', B" |
| 40 ml Suction | 35 ml Suction | Step C, C', C" |
| 40 ml Discharge | 35 ml Discharge | Step D, D', D" |
| 45 ml Suction | 40 ml Suction | Step E, E', E" (first) |
| 45 ml Discharge | 40 ml Discharge | |
| 50 ml Suction | 45 ml Suction | Step E, E', E" (second) |
| 50 ml Discharge | 45 ml Discharge | |
| 52.5 ml Suction | 50 ml Suction | Step E, E', E" (third) |
| 52.5 ml Discharge | 50 ml Discharge | |
| 55 ml Suction | 52.5 ml Suction | Step E, E', E" (fourth) |
| 55 ml Discharge | 52.5 ml Discharge | |
| 57.5 ml Suction | 55 ml Suction | Step E, E', E" (fifth) |
| 57.5 ml Discharge | 55 ml Discharge | |
| 60 ml Suction | 57.5 ml Suction | Step E, E', E" (sixth) |
| 60 ml Discharge | 57.5 ml Discharge | |
| | 60 ml Suction | Step F, F', F" |
| | 60 ml Discharge | Step G, G', G" |
| total 395 ml | total 395 ml | |

TABLE 4

<Setting 3 (large uterine size; perfusion operation, 8 times)>

| Syringe I | Syringe II | |
|---|---|---|
| 45 ml Suction | | Step A, A', A" |
| 45 ml Discharge | | Step B, B', B" |
| 50 ml Suction | 45 ml Suction | Step C, C', C" |
| 50 ml Discharge | 45 ml Discharge | Step D, D', D" |
| 55 ml Suction | 50 ml Suction | Step E, E', E" (first) |
| 55 ml Discharge | 50 ml Discharge | |
| 60 ml Suction | 55 ml Suction | Step E, E', E" (second) |
| 60 ml Discharge | 55 ml Discharge | |
| 62.5 ml Suction | 60 ml Suction | Step E, E', E" (third) |
| 62.5 ml Discharge | 60 ml Discharge | |
| 65 ml Suction | 62.5 ml Suction | Step E, E', E" (fourth) |
| 65 ml Discharge | 62.5 ml Discharge | |
| 67.5 ml Suction | 65 ml Suction | Step E, E', E" (fifth) |
| 67.5 ml Discharge | 65 ml Discharge | |
| 70 ml Suction | 67.5 ml Suction | Step E, E', E" (sixth) |
| 70 ml Discharge | 67.5 ml Discharge | |
| | 70 ml Suction | Step F, F', F" |
| | 70 ml Discharge | Step G, G', G" |
| total 475 ml | total 475 ml | |

TABLE 5

<Setting 4 (extra-large uterine size; perfusion operation, 8 times)>

| Syringe I | Syringe II | |
|---|---|---|
| 55 ml Suction | | Step A, A', A" |
| 55 ml Discharge | | Step B, B', B" |
| 60 ml Suction | 55 ml Suction | Step C, C', C" |
| 60 ml Discharge | 55 ml Discharge | Step D, D', D" |

TABLE 5-continued

<Setting 4 (extra-large uterine size; perfusion operation, 8 times)>

| Syringe I | Syringe II | |
|---|---|---|
| 65 ml Suction | 60 ml Suction | Step E, E', E" (first) |
| 65 ml Discharge | 60 ml Discharge | |
| 70 ml Suction | 65 ml Suction | Step E, E', E" (second) |
| 70 ml Discharge | 65 ml Discharge | |
| 72.5 ml Suction | 70 ml Suction | Step E, E', E" (third) |
| 72.5 ml Discharge | 70 ml Discharge | |
| 75 ml Suction | 72.5 ml Suction | Step E, E', E" (fourth) |
| 75 ml Discharge | 72.5 ml Discharge | |
| 77.5 ml Suction | 75 ml Suction | Step E, E', E" (fifth) |
| 77.5 ml Discharge | 75 ml Discharge | |
| 80 ml Suction | 77.5 ml Suction | Step E, E', E" (sixth) |
| 80 ml Discharge | 77.5 ml Discharge | |
| | 80 ml Suction | Step F, F', F" |
| | 80 ml Discharge | Step G, G', G" |
| total 555 ml | total 555 ml | |

The apparatus of the present invention may be configured such that the perfusion operation can be carried out according to a pattern modified from a pre-set pattern described above. For example, the apparatus may be configured such that: when selecting Setting 4 and inputting change of the frequency of the perfusion operation to 5 times, the operation of the syringe I is completed after suction-discharge of 72.5 ml of the perfusate in Step E, E', or E" (third perfusion); the 72.5 ml suction by the syringe II is performed as Step F, F', or F": the 72.5 ml discharge by the syringe II is performed as Step G, G', or G"; and then the operation of the syringe II is completed to complete the perfusion operations. Or, for example, the apparatus may be configured such that, when selecting Setting 4 and inputting change of the liquid volume by −5 ml, the apparatus can perform the perfusion operations with all the liquid volumes presented in Table 5 changed by −5 ml.

The apparatus of the present invention is equipped with a program to cause a computer of the apparatus to carry out each step (Step A, A', or A" to Step G, G', or G") of the control method described above. This program causes operations of the syringe pump control section and the liquid transfer direction control section (in cases of the first mode and the second mode) of the apparatus in a coordinated manner, to carry out each step of the control method described above. Patterns of the volume of the liquid sucked/discharged such as those exemplified in Tables 2 to 5 may also be installed as a program on the apparatus.

In the method of collecting an embryo(s) in a livestock uterus using the apparatus of the present invention, first, the apparatus is brought into a state where a balloon catheter inserted into a livestock uterus is connected to the balloon catheter connection section; the tip of the liquid transfer line section I-i is connected to the perfusate supply section; and the liquid transfer line section II-ii is connected to the embryo collection section (Step 1). The balloon catheter may be inserted into the uterus, and air may be sent into the balloon to inflate the balloon, to thereby fix the balloon in the left or right uterine horn, followed by connecting the balloon catheter to the balloon catheter connection section of the apparatus.

Subsequently, the following Steps 2 to 8 are carried out.

Step 2 of sucking the perfusate from the perfusate supply section into the syringe I, in a state where the flow of the perfusate from the livestock uterus toward the syringe I is prevented (which corresponds to the Steps A, A', A" described above).

Step 3 of injecting the perfusate from the syringe I into the livestock uterus through the balloon catheter, in a state where the flow of the perfusate from the syringe I toward the perfusate supply section is prevented (which corresponds to the Steps B, B', B").

Step 4 of sucking the perfusate into the syringe I in a state where the flow of the perfusate from the livestock uterus toward the syringe I is prevented, and, in parallel, collecting the perfusate in the livestock uterus with the syringe II through the balloon catheter in a state where the flow of the perfusate from the embryo collection section toward the syringe II is prevented (which corresponds to the Steps C. C' C").

Step 5 of injecting the perfusate from the syringe I into the livestock uterus through the balloon catheter in a state where the flow of the perfusate from the syringe I toward the perfusate supply section is prevented, and, in parallel, discharging the perfusate collected in the syringe II into the embryo collection section in a state where the flow of the perfusate from the syringe II toward the livestock uterus is prevented (which corresponds to the Steps D, D', D").

Step 6 of further carrying out Step 4 and Step 5 at least once (which corresponds to the Steps E, E', E").

Step 7 of collecting the perfusate in the livestock uterus with the syringe II through the balloon catheter, in a state where the flow of the perfusate from the embryo collection section toward the syringe II is prevented (which corresponds to the Steps F, F', F").

Step 8 of discharging the perfusate collected in the syringe II into the embryo collection section, in a state where the flow of the perfusate from the syringe II toward the livestock uterus is prevented (which corresponds to the Steps G, G', G").

Step 6 (Step 4+Step 5), which corresponds to the Steps E, E', E", is preferably carried out twice or more times, for example, about twice to 8 times, twice to 6 times, or 4 to 6 times, as described above.

EXAMPLES

A livestock embryo collection apparatus having the configuration shown in FIG. 1 was prepared employing pinch valves as the liquid transfer direction control section. A balloon catheter for cattle was connected to the apparatus, and embryos were collected from the uterus of living cattle. The working time and the collection accuracy were compared with those in a conventional embryo collection method which was based on the intrauterine circulatory perfusion method (a perfusate was injected into the uterus by the gravity drop method; Non-Patent Document 1). An experienced veterinarian with over 20-year experience of embryo collection carried out the conventional method, and a collection method using the apparatus of the present invention. For the collection method using the apparatus of the present invention, a setting was selected from those presented in Table 2 to Table 5 above in accordance with the uterine size of the cattle.

(Working Time)

In the conventional method, the time required for the process from placement of the balloon catheter in the uterus to completion of perfusion in the right and left uterine horns in each individual was 18 minutes to 42 minutes (number of individuals tested: 35). In contrast, when the apparatus of the present invention was utilized, the time required for each individual was 8 minutes to less than 14 minutes (number of individuals tested: 35), indicating that the required time could be largely reduced.

By using the apparatus of the present invention, a large number of embryos can be practically collected by a small number of workers. It can be said that the time required in the conventional method was short in the present test since the collection operation was carried out by the highly skilled, experienced embryo collection technician. A longer time will be required for veterinarians with a common level of skill when embryos are collected by the conventional method. In contrast, when the apparatus of the present invention is used, after the insertion and fixation of the balloon catheter, the two syringe pumps work in conjunction with each other to simultaneously carry out suction and simultaneously carry out discharge, thereby automatically collecting embryos. Thus, the apparatus of the present invention enables embryo collection in a very short time without being largely influenced by the proficiency in the embryo collection technique.

(Collection Accuracy)

After collection of embryos with the apparatus of the present invention, the conventional collection method was carried out by an experienced operator. As a result, no embryo could be collected. This result suggests that, by the collection method using the apparatus of the present invention, embryos could be collected in a very short time with the same accuracy as that achieved by a skilled technician.

DESCRIPTION OF SYMBOLS

10 Livestock embryo collection apparatus
20 Syringe I
30 Syringe II
210 Liquid transfer line I
211 Liquid transfer line section I-i
212 Liquid transfer line section I-ii
310 Liquid transfer line II
311 Liquid transfer line section II-i
312 Liquid transfer line section II-ii
40, 40' Syringe pump control section
50 Liquid transfer direction control section
60 Balloon catheter connection section
70, 70', 70" Input section
80, 80' Display section

The invention claimed is:

1. A livestock embryo collection apparatus comprising:
a syringe I configured to suck a perfusate from a perfusate supply section and injecting the perfusate into a livestock uterus;
a liquid transfer line I which is connected to the syringe I and bifurcated, comprising: a liquid transfer line section I-i configured for connection to the perfusate supply section; and a liquid transfer line section I-ii configured for connection to a balloon catheter;
a syringe II configured to collect the perfusate injected into the livestock uterus and discharge the perfusate into an embryo collection section;
a liquid transfer line II which is connected to the syringe II and bifurcated, comprising: a liquid transfer line section II-i configured for connection to the balloon catheter; and a liquid transfer line section II-ii configured for connection to the embryo collection section;
a liquid transfer direction control section configured to control a direction of transfer of the perfusate in the liquid transfer lines;
a syringe pump control section configured to control pump operation of the syringe I and the syringe II; and
an input section for a user to input an instruction;
wherein the liquid transfer line section I-ii and the liquid transfer line section II-i join together to provide a balloon catheter connection section at a tip thereof.

2. The apparatus according to claim 1, wherein the syringe pump control section carries out an operation of sucking the perfusate from the perfusate supply section by the syringe I and an operation of collecting the perfusate from the livestock uterus by the syringe II in parallel, and carries out an operation of injecting the perfusate into the livestock uterus by the syringe I and an operation of discharging the collected perfusate into the embryo collection section by the syringe II in parallel.

3. The apparatus according to claim 1, wherein the livestock is a large mammal.

4. The apparatus according to claim 1, wherein the livestock is cattle.

5. The apparatus according to claim 1, wherein the liquid transfer direction control section comprises: a shut-off valve provided for each of the liquid transfer line section I-i, liquid transfer line section I-ii, liquid transfer line section II-i, and liquid transfer line section II-ii; and a valve control section configured to control opening and closing of the shut-off valves.

6. A method of controlling the livestock embryo collection apparatus according to claim 5, the method comprising:
Step A of carrying out a sucking operation of the syringe I without operating the syringe II, in a state where: the shut-off valve for the liquid transfer line section I-i is opened; and the shut-off valve for the liquid transfer line section I-ii is closed;
Step B of carrying out a discharging operation of the syringe I without operating the syringe II, in a state where: the shut-off valve for the liquid transfer line section I-i is closed; and the shut-off valve for the liquid transfer line section I-ii is opened;
Step C of carrying out a sucking operation of the syringe I and a sucking operation of the syringe II in parallel, in a state where: the shut-off valve for the liquid transfer line section I-i is opened; the shut-off valve for the liquid transfer line section I-ii is closed; the shut-off valve for the liquid transfer line section II-i is opened; and the shut-off valve for the liquid transfer line section II-ii is closed;
Step D of carrying out a discharging operation of the syringe I and a discharging operation of the syringe II in parallel, in a state where: the shut-off valve for the liquid transfer line section I-i is closed; the shut-off valve for the liquid transfer line section I-ii is opened; the shut-off valve for the liquid transfer line section II-i is closed; and the shut-off valve for the liquid transfer line section II-ii is opened;
Step E of carrying out Step C and Step D again, which Step E is carried out at least once;
Step F of carrying out a sucking operation of the syringe II without operating the syringe I, in a state where: the shut-off valve for the liquid transfer line section II-i is opened; and the shut-off valve for the liquid transfer line section II-ii is closed; and
Step G of carrying out a discharging operation of the syringe II without operating the syringe I, in a state where: the shut-off valve for the liquid transfer line section II-i is closed; and the shut-off valve for the liquid transfer line section II-ii is opened.

7. The method according to claim 6, wherein Step E, E', or E" is carried out at least twice.

8. The method according to claim 7, wherein the volumes of liquid sucked and discharged by the syringes are selected from the following Setting 1 to Setting 4 according to an instruction from a user to carry out each step:

<Setting 1>
- (1) in Step A, A', or A", the syringe I sucks 25 ml±5 ml of perfusate;
- (2) in Step B, B', or B", the syringe I discharges 25 ml±5 ml of perfusate;
- (3) in Step C, C', or C", the syringe I sucks 30 ml±5 ml of perfusate, and the syringe II sucks 25 ml±5 ml of perfusate;
- (4) in Step D, D', or D", the syringe I discharges 30 ml±5 ml of perfusate, and the syringe II discharges 25 ml±5 ml of perfusate;
- (5) in Step E, E', or E",
  - (5-1) the syringe I sucks 35 ml±5 ml of perfusate, and the syringe II sucks 30 ml±5 ml of perfusate;
  - (5-2) the syringe I discharges 35 ml±5 ml of perfusate, and the syringe II discharges 30 ml±5 ml of perfusate;
  - (5-3) the syringe I sucks 40 ml±5 ml of perfusate, and the syringe II sucks 35 ml±5 ml of perfusate;
  - (5-4) the syringe I discharges 40 ml±5 ml of perfusate, and the syringe II discharges 35 ml±5 ml of perfusate;
  - (5-5) the syringe I sucks 42.5 ml±5 ml of perfusate, and the syringe II sucks 40 ml±5 ml of perfusate;
  - (5-6) the syringe I discharges 42.5 ml±5 ml of perfusate, and the syringe II discharges 40 ml±5 ml of perfusate;
  - (5-7) the syringe I sucks 45 ml±5 ml of perfusate, and the syringe II sucks 42.5 ml±5 ml of perfusate;
  - (5-8) the syringe I discharges 45 ml±5 ml of perfusate, and the syringe II discharges 42.5 ml±5 ml of perfusate;
  - (5-9) the syringe I sucks 47.5 ml±5 ml of perfusate, and the syringe II sucks 45 ml±5 ml of perfusate;
  - (5-10) the syringe I discharges 47.5 ml±5 ml of perfusate, and the syringe II discharges 45 ml±5 ml of perfusate;
  - (5-11) the syringe I sucks 50 ml±5 ml of perfusate, and the syringe II sucks 47.5 ml±5 ml of perfusate;
  - (5-12) the syringe I discharges 50 ml±5 ml of perfusate, and the syringe II discharges 47.5 ml±5 ml of perfusate;
- (6) in Step F, F', or F", the syringe II sucks 50 ml±5 ml of perfusate;
- (7) in Step G, G', or G", the syringe II discharges 50 ml±5 ml of perfusate;

<Setting 2>
- (1) in Step A, A', or A", the syringe I sucks 35 ml±5 ml of perfusate;
- (2) in Step B, B', or B", the syringe I discharges 35 ml±5 ml of perfusate;
- (3) in Step C, C', or C", the syringe I sucks 40 ml±5 ml of perfusate, and the syringe II sucks 35 ml±5 ml of perfusate;
- (4) in Step D, D', or D", the syringe I discharges 40 ml±5 ml of perfusate, and the syringe II discharges 35 ml±5 ml of perfusate;
- (5) in Step E, E', or E",
  - (5-1) the syringe I sucks 45 ml±5 ml of perfusate, and the syringe II sucks 40 ml±5 ml of perfusate;
  - (5-2) the syringe I discharges 45 ml±5 ml of perfusate, and the syringe II discharges 40 ml±5 ml of perfusate;
  - (5-3) the syringe I sucks 50 ml±5 ml of perfusate, and the syringe II sucks 45 ml±5 ml of perfusate;
  - (5-4) the syringe I discharges 50 ml±5 ml of perfusate, and the syringe II discharges 45 ml±5 ml of perfusate;
  - (5-5) the syringe I sucks 52.5 ml±5 ml of perfusate, and the syringe II sucks 50 ml±5 ml of perfusate;
  - (5-6) the syringe I discharges 52.5 ml±5 ml of perfusate, and the syringe II discharges 50 ml±5 ml of perfusate;
  - (5-7) the syringe I sucks 55 ml±5 ml of perfusate, and the syringe II sucks 52.5 ml±5 ml of perfusate;
  - (5-8) the syringe I discharges 55 ml±5 ml of perfusate, and the syringe II discharges 52.5 ml±5 ml of perfusate;
  - (5-9) the syringe I sucks 57.5 ml±5 ml of perfusate, and the syringe II sucks 55 ml±5 ml of perfusate;
  - (5-10) the syringe I discharges 57.5 ml±5 ml of perfusate, and the syringe II discharges 55 ml±5 ml of perfusate;
  - (5-11) the syringe I sucks 60 ml±5 ml of perfusate, and the syringe II sucks 57.5 ml±5 ml of perfusate;
  - (5-12) the syringe I discharges 60 ml±5 ml of perfusate, and the syringe II discharges 57.5 ml od perfusate;
- (6) in Step F, F', or F", the syringe II sucks 60 ml±5 ml of perfusate;
- (7) in Step G, G', or G", the syringe II discharges 60 ml±5 ml of perfusate;

<Setting 3>
- (1) in Step A, A', or A", the syringe I sucks 45 ml±5 ml of perfusate;
- (2) in Step B, B', or B", the syringe I discharges 45 ml±5 ml of perfusate;
- (3) in Step C, C', or C", the syringe I sucks 50 ml±5 ml of perfusate, and the syringe II sucks 45 ml±5 ml of perfusate;
- (4) in Step D, D', or D", the syringe I discharges 50 ml±5 ml of perfusate, and the syringe II discharges 45 ml±5 ml of perfusate;
- (5) in Step E, E', or E",
  - (5-1) the syringe I sucks 55 ml±5 ml of perfusate, and the syringe II sucks 50 ml±5 ml of perfusate;
  - (5-2) the syringe I discharges 55 ml±5 ml of perfusate, and the syringe II discharges 50 ml±5 ml of perfusate;
  - (5-3) the syringe I sucks 60 ml±5 ml of perfusate, and the syringe II sucks 55 ml±5 ml of perfusate;
  - (5-4) the syringe I discharges 60 ml±5 ml of perfusate, and the syringe II discharges 55 ml±5 ml of perfusate;
  - (5-5) the syringe I sucks 62.5 ml±5 ml of perfusate, and the syringe II sucks 60 ml±5 ml of perfusate;
  - (5-6) the syringe I discharges 62.5 ml±5 ml of perfusate, and the syringe II discharges 60 ml±5 ml of perfusate;
  - (5-7) the syringe I sucks 65 ml±5 ml of perfusate, and the syringe II sucks 62.5 ml±5 ml of perfusate;
  - (5-8) the syringe I discharges 65 ml±5 ml of perfusate, and the syringe II discharges 62.5 ml±5 ml of perfusate
  - (5-9) the syringe I sucks 67.5 ml±5 ml of perfusate, and the syringe II sucks 65 ml±5 ml of perfusate;
  - (5-10) the syringe I discharges 67.5 ml±5 ml of perfusate, and the syringe II discharges 65 ml±5 ml of perfusate;
  - (5-11) the syringe I sucks 70 ml±5 ml of perfusate, and the syringe II sucks 67.5 ml±5 ml of perfusate;

(5-12) the syringe I discharges 70 ml±5 ml of perfusate, and the syringe II discharges 67.5 ml±5 ml of perfusate;

(6) in Step F, F', or F", the syringe II sucks 70 ml±5 ml of perfusate;

(7) in Step G, G', or G", the syringe II discharges 70 ml±5 ml of perfusate;

<Setting 4>

(1) in Step A, A', or A", the syringe I sucks 55 ml±5 ml of perfusate;

(2) in Step B, B', or B", the syringe I discharges 55 ml±5 ml of perfusate;

(3) in Step C, C', or C", the syringe I sucks 60 ml±5 ml of perfusate, and the syringe II sucks 55 ml±5 ml of perfusate;

(4) in Step D, D', or D", the syringe I discharges 60 ml±5 ml of perfusate, and the syringe II discharges 55 ml±5 ml of perfusate;

(5) in Step E, E', or E", (5-1) the syringe I sucks 65 ml±5 ml of perfusate, and the syringe II sucks 60 ml±5 ml of perfusate;

(5-2) the syringe I discharges 65 ml±5 ml of perfusate, and the syringe II discharges 60 ml±5 ml of perfusate;

(5-3) the syringe I sucks 70 ml±5 ml of perfusate, and the syringe II sucks 65 ml±5 ml of perfusate;

(5-4) the syringe I discharges 70 ml±5 ml of perfusate, and the syringe II discharges 65 ml±5 ml of perfusate;

(5-5) the syringe I sucks 72.5 ml±5 ml of perfusate, and the syringe II sucks 70 ml±5 ml of perfusate;

(5-6) the syringe I discharges 72.5 ml±5 ml of perfusate, and the syringe II discharges 70 ml±5 ml of perfusate;

(5-7) the syringe I sucks 75 ml±5 ml of perfusate, and the syringe II sucks 72.5 ml±5 ml of perfusate;

(5-8) the syringe I discharges 75 ml±5 ml of perfusate, and the syringe II discharges 72.5 ml±5 ml of perfusate;

(5-9) the syringe I sucks 77.5 ml±5 ml of perfusate, and the syringe II sucks 75 ml±5 ml of perfusate;

(5-10) the syringe I discharges 77.5 ml±5 ml of perfusate, and the syringe II discharges 75 ml±5 ml of perfusate;

(5-11) the syringe I sucks 80 ml±5 ml of perfusate, and the syringe II sucks 77.5 ml±5 ml of perfusate;

(5-12) the syringe I discharges 80 ml±5 ml of perfusate, and the syringe II discharges 77.5 ml±5 ml of perfusate;

(6) in Step F, F', or F", the syringe II sucks 80 ml±5 ml of perfusate;

(7) in Step G, G', or G", the syringe II discharges 80 ml±5 ml of perfusate.

9. The apparatus according to claim 1, wherein the liquid transfer direction control section comprises: a three-way stopcock I and a three-way stopcock II provided for the bifurcated portion of the liquid transfer line I and the bifurcated portion of the liquid transfer line II, respectively; and a three-way stopcock control section configured to control the direction of each three-way stopcock.

10. A method of controlling the livestock embryo collection apparatus according to claim 9, the method comprising:

Step A' of carrying out a sucking operation of the syringe I without operating the syringe II, in a state where the three-way stopcock I allows liquid transfer between the syringe I and the liquid transfer line section I-i, and blocks liquid transfer between the syringe I and the liquid transfer line section I-ii;

Step B' of carrying out a discharging operation of the syringe I without operating the syringe II, in a state where the three-way stopcock I blocks liquid transfer between the syringe I and the liquid transfer line section I-i, and allows liquid transfer between the syringe I and the liquid transfer line section I-ii;

Step C' of carrying out a sucking operation of the syringe I and a sucking operation of the syringe II in parallel, in a state where the three-way stopcock I allows liquid transfer between the syringe I and the liquid transfer line section I-i, and blocks liquid transfer between the syringe I and the liquid transfer line section I-ii, and where the three-way stopcock II allows liquid transfer between the syringe II and the liquid transfer line section II-i, and blocks liquid transfer between the syringe II and the liquid transfer line section II-ii;

Step D' of carrying out a discharging operation of the syringe I and a discharging operation of the syringe II in parallel, in a state where the three-way stopcock I blocks liquid transfer between the syringe I and the liquid transfer line section I-i, and allows liquid transfer between the syringe I and the liquid transfer line section I-ii, and where the three-way stopcock II blocks liquid transfer between the syringe II and the liquid transfer line section II-i, and allows liquid transfer between the syringe II and the liquid transfer line section II-ii;

Step E' of carrying out Step C' and Step D' again, which Step E' is carried out at least once;

Step F' of carrying out a sucking operation of the syringe II without operating the syringe I, in a state where the three-way stopcock II allows liquid transfer between the syringe II and the liquid transfer line section II-i, and blocks liquid transfer between the syringe II and the liquid transfer line section II-ii; and Step G' of carrying out a discharging operation of the syringe II without operating the syringe I, in a state where the three-way stopcock II blocks liquid transfer between the syringe II and the liquid transfer line section II-i, and allows liquid transfer between the syringe II and the liquid transfer line section II-ii.

11. The apparatus according to claim 1, wherein the liquid transfer direction control section comprises a check valve provided for each of the liquid transfer line section I-i, liquid transfer line section I-ii, liquid transfer line section II-i, and liquid transfer line section II-ii.

12. A method of controlling the livestock embryo collection apparatus according to claim 11, the method comprising:

Step A" of carrying out a sucking operation of the syringe I without operating the syringe II;

Step B" of carrying out a discharging operation of the syringe I without operating the syringe II;

Step C" of carrying out a sucking operation of the syringe I and a sucking operation of the syringe II in parallel;

Step D" of carrying out a discharging operation of the syringe I and a discharging operation of the syringe II in parallel;

Step E" of carrying out Step C" and Step D" again, which Step E" is carried out at least once;

Step F" of carrying out a sucking operation of the syringe II without operating the syringe I; and Step G" of carrying out a discharging operation of the syringe II without operating the syringe I.

13. A method of collecting an embryo(s) in a livestock uterus, the method comprising:
- Step 1 of bringing the apparatus according to claim 1 into a state where: the balloon catheter inserted into the livestock uterus is connected to the balloon catheter connection section; the tip of the liquid transfer line section I-i is connected to the perfusate supply section; and the tip of the liquid transfer line section II-ii is connected to the embryo collection section;
- Step 2 of sucking the perfusate from the perfusate supply section into the syringe I, in a state where a flow of the perfusate from the livestock uterus toward the syringe I is prevented;
- Step 3 of injecting the perfusate from the syringe I into the livestock uterus through the balloon catheter, in a state where the flow of the perfusate from the syringe I toward the perfusate supply section is prevented;
- Step 4 of sucking the perfusate into the syringe I in a state where the flow of the perfusate from the livestock uterus toward the syringe I is prevented, and, in parallel, collecting the perfusate in the livestock uterus with the syringe II through the balloon catheter in a state where the flow of the perfusate from the embryo collection section toward the syringe II is prevented;
- Step 5 of injecting the perfusate from the syringe I into the livestock uterus through the balloon catheter in a state where the flow of the perfusate from the syringe I toward the perfusate supply section is prevented, and, in parallel, discharging the collected perfusate in the syringe II into the embryo collection section, in a state where the flow of the perfusate from the syringe II toward the livestock uterus is prevented;
- Step 6 of further carrying out Step 4 and Step 5 at least once;
- Step 7 of collecting the perfusate in the livestock uterus with the syringe II through the balloon catheter, in a state where the flow of the perfusate from the embryo collection section toward the syringe II is prevented; and
- Step 8 of discharging the perfusate collected in the syringe II into the embryo collection section, in a state where the flow of the perfusate from the syringe II toward the livestock uterus is prevented.

* * * * *